United States Patent
Cobb et al.

(10) Patent No.: US 9,492,157 B2
(45) Date of Patent: Nov. 15, 2016

(54) BONE ANCHOR APPARATUS AND METHOD

(71) Applicants: Tyson Cobb, Bettendorf, IA (US); Alejandro Badia, Miami, FL (US); Stacey Berner, Reisterstown, MD (US); Steven Topper, Colorado Springs, CO (US); Vincent van Donck, San Diego, CA (US)

(72) Inventors: Tyson Cobb, Bettendorf, IA (US); Alejandro Badia, Miami, FL (US); Stacey Berner, Reisterstown, MD (US); Steven Topper, Colorado Springs, CO (US); Vincent van Donck, San Diego, CA (US)

(73) Assignee: American Hand Institute, LLC, Rochester, NY (US)

( * ) Notice: Subject to any disclaimer, the term of this patent is extended or adjusted under 35 U.S.C. 154(b) by 66 days.

(21) Appl. No.: 13/732,730

(22) Filed: Jan. 2, 2013

(65) Prior Publication Data
US 2014/0188166 A1    Jul. 3, 2014

(51) Int. Cl.
*A61B 17/04*    (2006.01)

(52) U.S. Cl.
CPC .... *A61B 17/0401* (2013.01); *A61B 2017/0414* (2013.01); *A61B 2017/0417* (2013.01)

(58) Field of Classification Search
CPC .................. A61B 17/0487; A61B 2017/0406; A61B 2017/0404; A61B 17/0401
USPC .................................. 606/30, 232, 300, 330
See application file for complete search history.

(56) References Cited

U.S. PATENT DOCUMENTS

| | | | |
|---|---|---|---|
| 6,066,141 A * | 5/2000 | Dall | A61B 17/82 606/281 |
| 7,887,551 B2 * | 2/2011 | Bojarski et al. | 606/139 |
| 2012/0310279 A1 * | 12/2012 | Sikora et al. | 606/232 |

* cited by examiner

*Primary Examiner* — Thomas McEvoy
(74) *Attorney, Agent, or Firm* — Joseph R. Englander

(57) ABSTRACT

A device and method is provided for a new and improved device for attaching tendon to bone wherein the intramedullary bone anchor, comprising a top section, a bottom section, a center section, a first end having a top inner portion and a top outer portion, a second end having a top inner portion and a top outer portion, and at least two holes extending from the top section through the bottom section, wherein the first end and second end are tapered and have seating geometry. The bone anchor is generally crescent-shaped or cylindrical.

13 Claims, 7 Drawing Sheets

BONE ANCHOR APPARATUS AND METHOD

CROSS-REFERENCE TO RELATED APPLICATION

This application relates to the same subject matter as co-pending provisional patent application Ser. No. 61/582,647, filed by the same applicant on Jan. 3, 2012. This application claims the Jan. 3, 2012 filing date as to the common subject matter.

BACKGROUND OF THE INVENTION

1. Field of Invention

The present invention relates to the medical arts. It is an apparatus, method and device used for anchoring a tendon, tissue, graft or prosthetic to a bone.

2. Background of Invention

There are numerous instances in the medical arts where it is necessary to anchor a tendon or other soft tissue to a bone. For example, an individual who tears a tendon away from the bone may have surgery to reattach said tendon to said bone.

The invention allows a surgeon to attach a patient's tendon to the patient's bone in a more efficient and secure manner than previously allowed.

SUMMARY OF THE INVENTION

In accordance with one aspect of the invention, a device for attaching a tendon to a bone is provided. The device includes an anchor with a suture or other medical thread.

In accordance with another aspect of the invention, the suture or medical thread passes from the top side of the anchor to the bottom side of the anchor through a hole passing through the width of the anchor. The thread then passes from the bottom of the anchor to the top of the anchor through a second hole passing through the width of the anchor, such that the suture or medical thread forms a loop with the ends of the suture or medical thread being used to attach to the tendon and pull the tendon to the anchor.

In accordance with yet another aspect of the invention, the anchor may be in a variety of shapes including a crescent shape or a bar shape with the holes for accommodating the suture or medical thread being recessed into the body of the anchor.

In accordance with yet another aspect of the invention, the anchor contains another hole or holes to provide a point of contact for an insertion device. The insertion device contacts the anchor at the hole or holes to allow the anchor to be securely inserted through an insertion hole drilled in the patient's bone.

The present invention provides for a new and improved device for attaching tendon to bone which overcome the above-referenced problems and others.

One advantage of the present invention is that the attachment of the tendon to the bone is more secure and allows the tendon to bear more force on the bone and have greater pullout strength compared with suture anchors.

Another advantage of the present invention is that it requires less invasion into the body and bone of the patient than devices described in the prior art. For example, the Endobutton requires a bicortical hole while the present invention requires only a unicortical hole, which will diminish the stress riser effect of a hole by 50-80%. This will also diminish the risk of iatrogenic fracture. Another advantage of a unicortical insertion is that the device can be inserted under direct visualization obviating the need for the intraoperative fluoroscopy required by other devices and thus minimizing radiation exposure during insertion.

Yet another advantage of the present invention is that it does not require any far side indirect procedures. This eliminates the possibility of far side soft tissue damage that is present with other devices.

Another advantage of the unicortical insertion of the present device is it minimizes the holes drilled in the patient's bones, minimizing drilling debris and reducing or eliminating the possibility of heterotopic ossification and synostosis. Additionally, fewer bone holes will result in less pain for the patient.

Yet another advantage of the present invention is that it allows for dynamic tensioning of the repair during surgery which is not possible with current devices. This will greatly facilitate the precision of the repair.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components. The drawings are only for purposes of illustrating preferred embodiments and are not to be construed as limiting the invention.

DETAILED DESCRIPTION OF THE INVENTION

Figure 1:
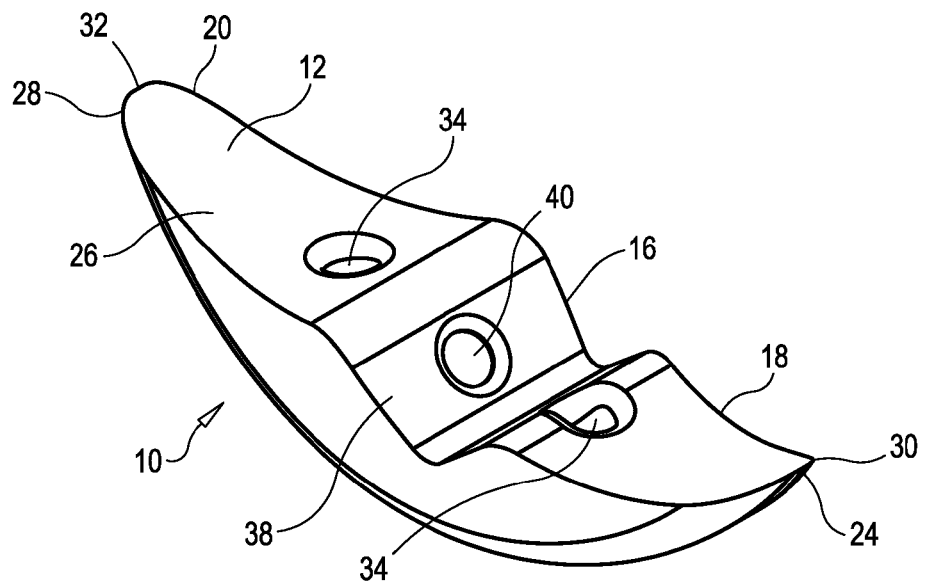
FIG. 1 is a top perspective view of an embodiment of the inventive device.
Figure 2:
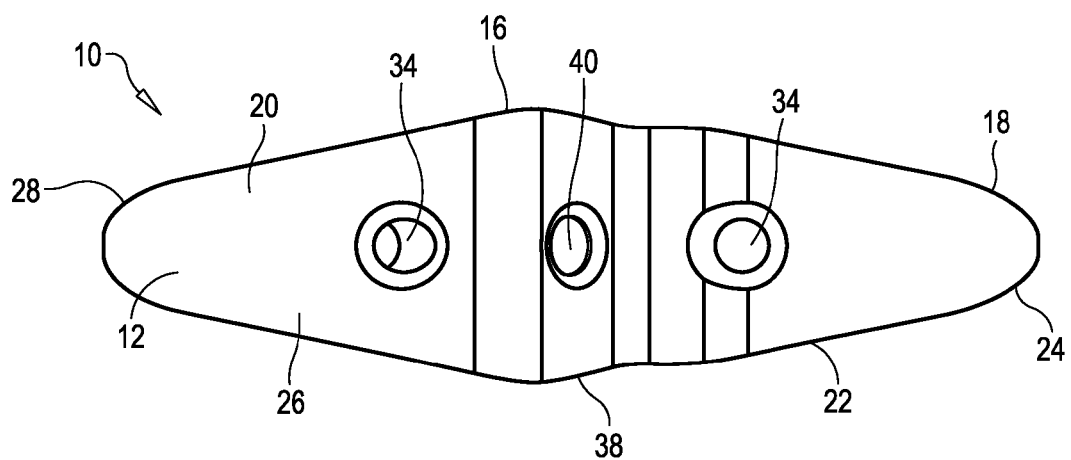
FIG. 2 is a top view of an embodiment of the inventive device.

FIG. 1 illustrates a device 10, in accordance with a particular embodiment of the present invention. The device 10 is an intramedullar bone anchor used to anchor, in a radius or other type of medullar bone, at least one of a tendon, muscle, graft, ligament and prosthetic so that it abuts a hole drilled in a bone and the periosteum around the hole. The device 100 may be constructed of titanium, ceramic, surgical steel, plastic, Kevlar, or other equivalent material known to those of ordinary skill in the art.

With reference to FIGS. 1-7, the intramedullary bone anchor of the present invention comprises a top section 12 and a bottom section 14 and a center section 16. The device 10 may be generally crescent shaped and includes a center section 16 between a first end 18 and a second end 20. A long axis to the device 10 runs between the first end 18 and the second end 20. The first end 18 includes a top inner portion 22 and a top outer portion 24. The second end 20 also has a top inner portion 26 and a top outer portion 28. As shown, the first end 18 may be tapered. Alternatively, the second end 20 may be tapered, or both ends may be tapered. Also, the first end top inner portion 22 and top outer portion 24 may be upwardly curved. The second end top inner portion 26 and top outer portion 28 may also be upwardly curved or both may be upwardly curved. The bottom section 14 may also be round or otherwise tapered.

The top outer portion of the first section may contain at least one point 30 on it. The point 30 may aid in seating the device 10 to the inner wall or endosteum of the medullar cavity of a bone. Alternatively, the top outer portion 24 may include several points, a jagged edge or other equivalent seating enhancing geometry known in the art. Alternatively, the top outer portion 28 of the second end 20 may include a point 32 or other seating enhancing geometry, or the top outer portion of both ends may each include a point or other seating enhancing geometry.

The device may also include at least two holes 34 from the top section 12 through the bottom section 14. These holes 34 are located generally at the center section 16 of the device 10. The holes 34 may be located along the long axis of the device 10. However, the holes 34 may be placed side by side or in other configurations known in the art.

Figure 3:
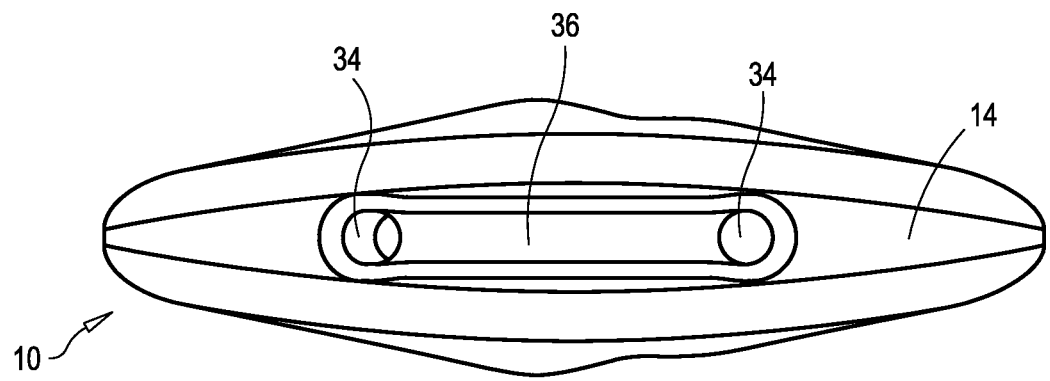
FIG. 3 is a bottom view of an embodiment of the inventive device.
Figure 4:
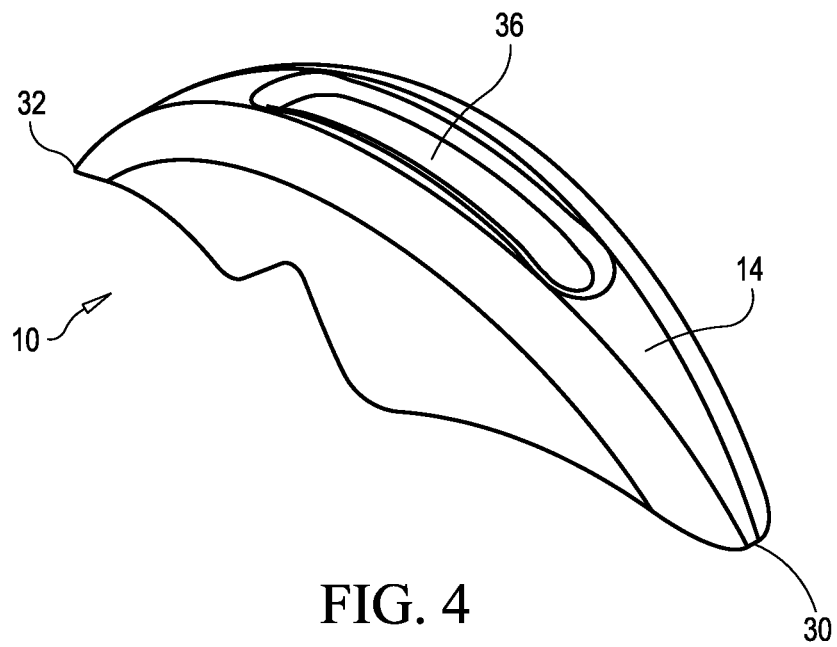
FIG. 4 is a bottom perspective view of an embodiment of the inventive device.
Figure 5:
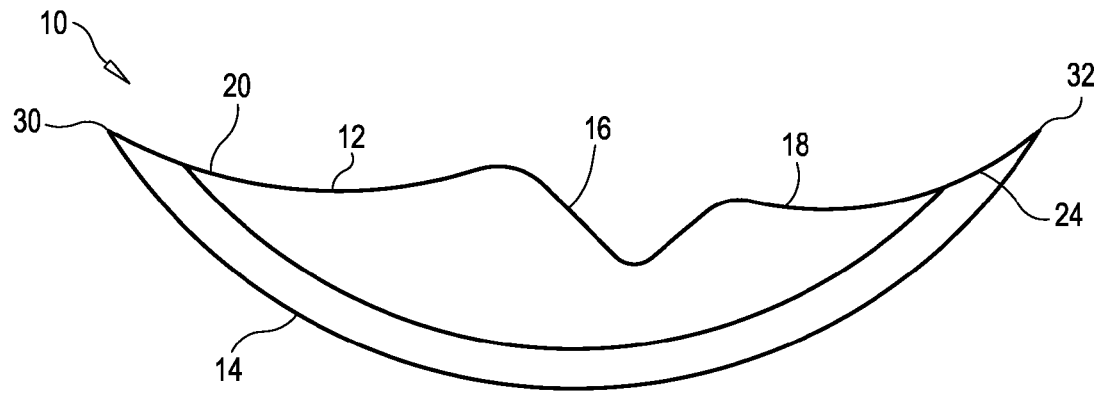
FIG. 5 is a side plan view of a first end an embodiment of the inventive device.
Figure 6:
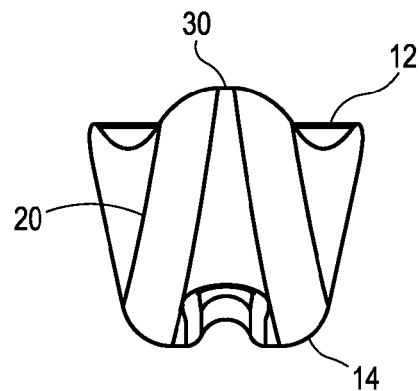
FIG. 6 is a front plan view of an embodiment of the inventive device.
Figure 7:
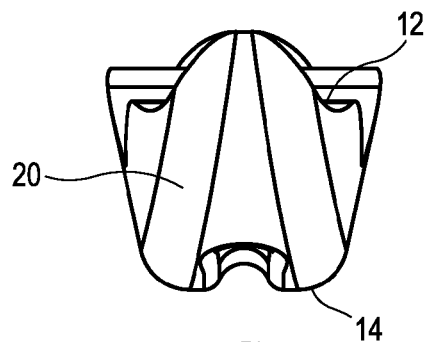
FIG. 7 is a rear plan view of an embodiment of the inventive device.
Figure 8:
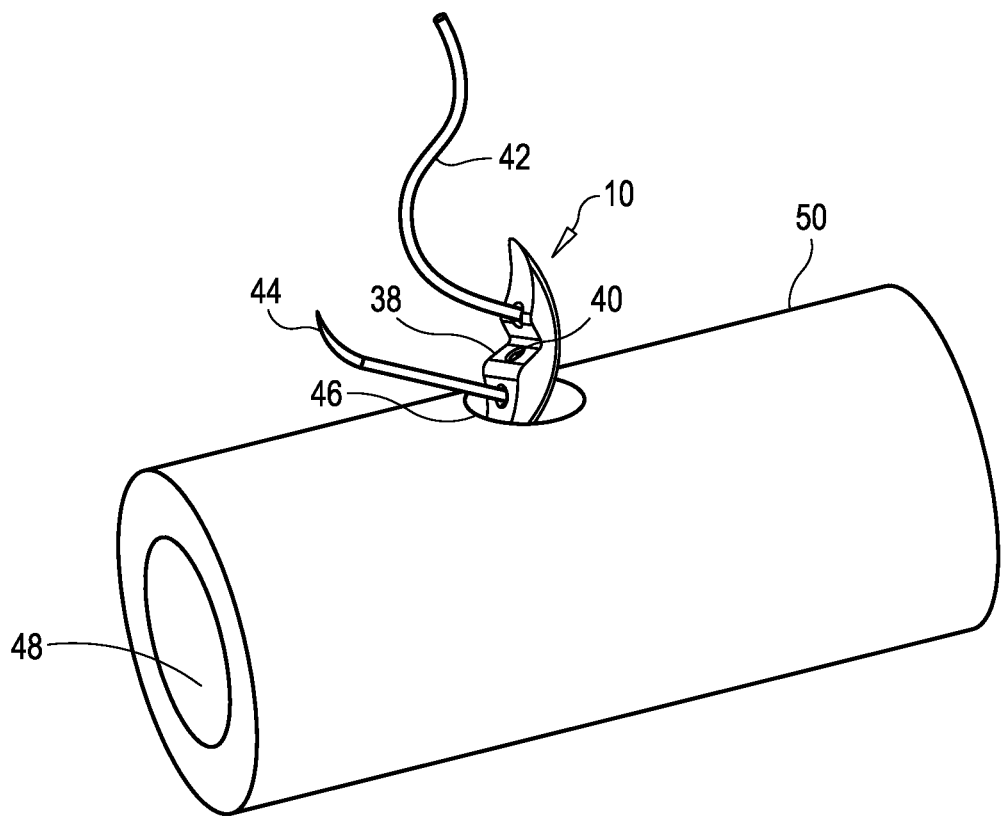
FIG. 8 is a perspective view of an embodiment of the inventive device in use after insertion.
Figure 9:
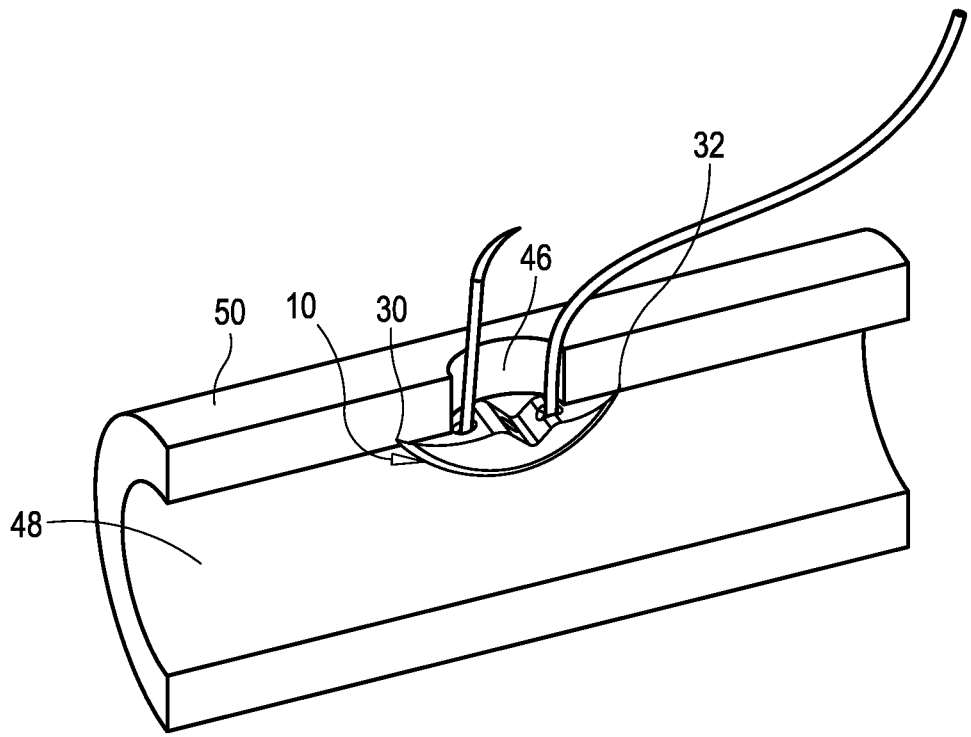
FIG. 9 is a split perspective view of an embodiment of the inventive device in use after insertion.
Figure 10A:
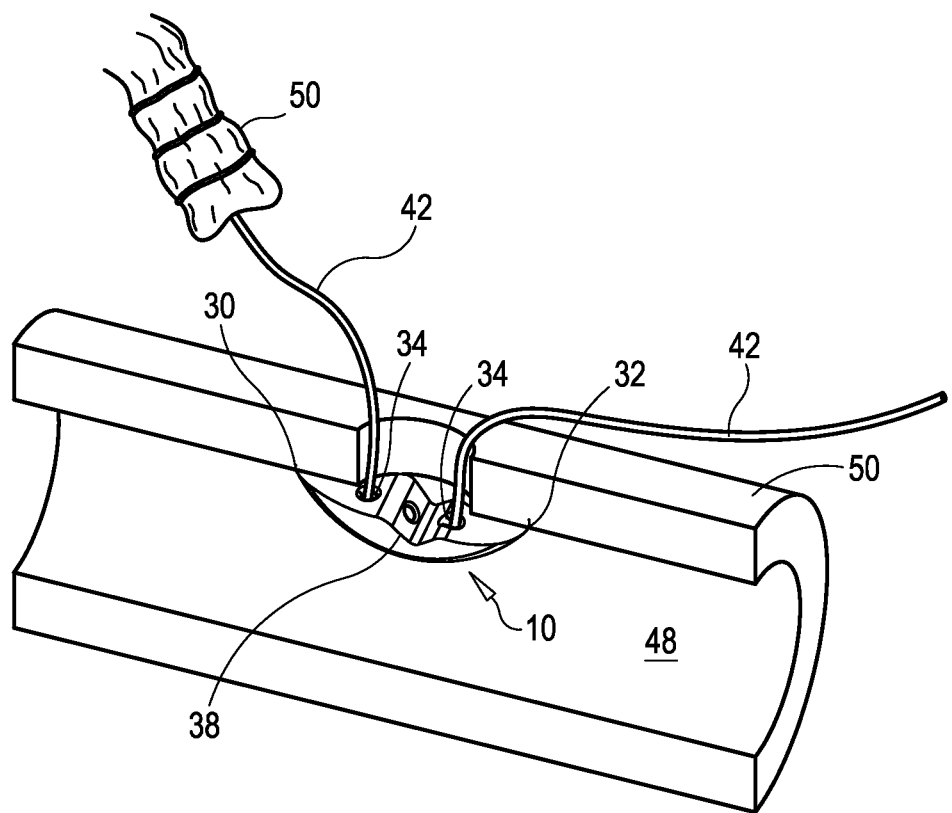
FIG. 10a is a split perspective view of an embodiment of the inventive device in use with a tendon attached to the suture.
Figure 10B:
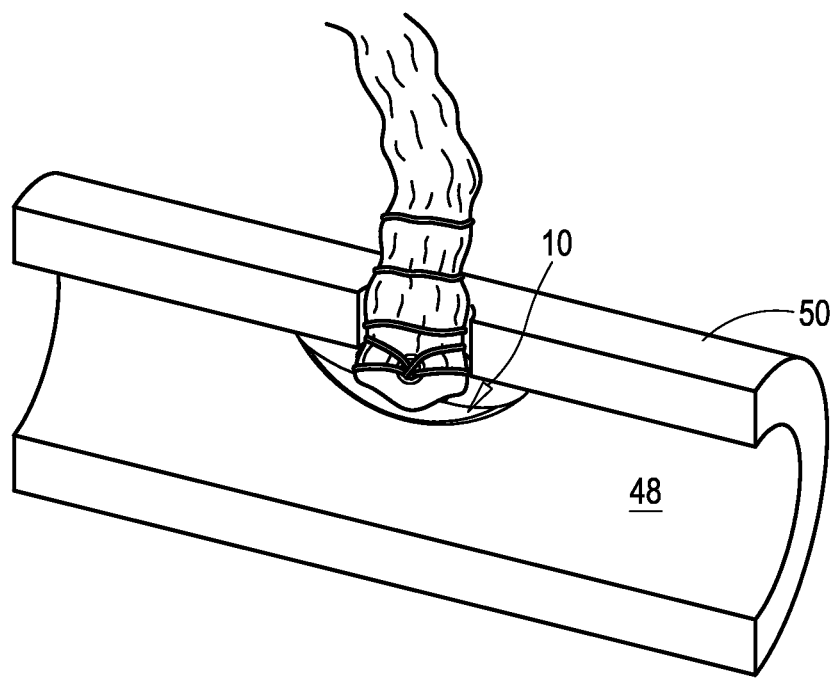
FIG. 10b is a perspective view of an embodiment of the inventive device in use with the suture pulled close to a medullar bone.

In addition, as shown in FIGS. 3 and 4, the device 10 may further include an indentation 36 on the bottom section 14 between the two holes 34. The indentation 36 may guide a needle used for suturing or to help ensure the placement or proper seating of suture material along the bottom section 14 of the device.

The device may also include an inserter surface 38 and/or an inserter indentation 40 located on the top section 12. The inserter surface 38 may include an inserter indentation 40 for seating an inserter tool. The inserter surface 38 may be angled. The angled surface may lie on an axis relative to the long axis of the device as shown in FIGS. 1, 2, 4 and 5, and may lie at an angle optimized for use of an inserter tool to position the device 10. The inserter surface 38 may be located on at least a portion of the center section 16. Other geometries for the inserter surface 38 and inserter indentation 40 known in the art are also contemplated. The inserter indentation 40 may have a geometry complementary to the geometry of the tip of the inserter tool to aid in control of the placement of the device.

The invention may be used as described herein and as shown in FIGS. 8, 9, 10a and 10b. An intramedullary bone anchor is provided. Suture material 42 may be attached to the bone anchor before use, using a suture needle 44. The needle may be size PS2 or P3 or other sizes known in the arts depending on the procedure being performed and the needs of the surgeon and patient. The suture material 42 may be inserted in a first hole through the device and returned through a second hole through the device. During use of the device, the suture material 42 may be guided by the indentation 36 along the bottom section 14 of the device. The suture may be made of fiberwire, ethibond, or other equivalent material known to those of ordinary skill in the art. The intramedullary bone anchor is inserted into an opening 46 into a medullar cavity 48 of a bone 50. An insertion tool may be used to place the device at, near or through the opening 46. The placement of the inserter tool on the intramedullary bone anchor may be guided by an inserter indentation 40. Once at least part of or all of the device is within the medullar cavity 48, the suture material 42 is pulled so that the one or more points on either or both ends of the device contact the inner wall or endosteum of the medullar cavity, so that the device may be seated against the inner wall or endosteum of the medullar cavity 48. The suture may then be attached to at least one of a tendon, muscle, ligament and prosthetic. Then the tendon may be pulled toward the opening 46 in the medullar cavity. The device 10 thus is used to anchor in a medullar bone, at least one of a tendon, muscle, graft, ligament and prosthetic so that it abuts a hole drilled in a bone and the periosteum around the hole.

Figure 11:
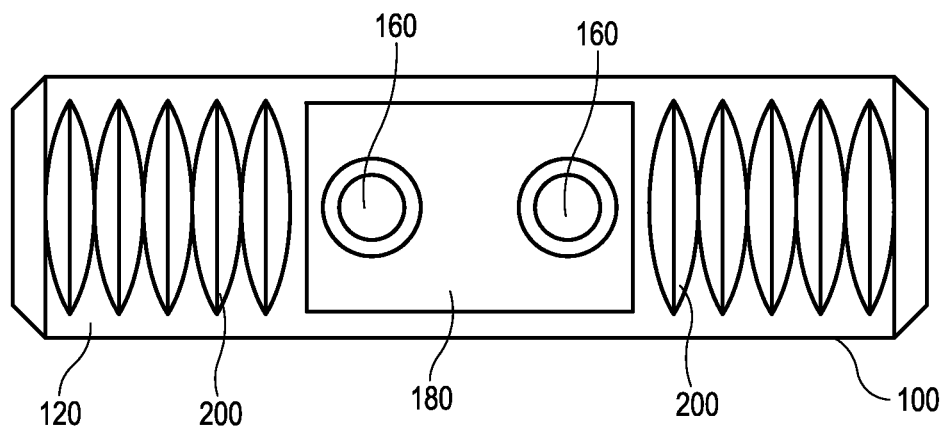
FIG. 11 is a top view of another embodiment of said device.

FIG. 11 illustrates another embodiment of a device 100, in accordance with the present invention. With reference to FIGS. 11-15, another embodiment of the intramedullar bone anchor of the present invention is shown, which comprises a top surface 120, a bottom surface 140, a plurality of holes 160, a center surface 180 comprising a generally flat surface, at least one irregularity in the top surface 200, a trench in the bottom surface 220, and an inserter indentation 240. The inserter indentation 240 may be on a first end 250 of the device 100. The device shown in FIGS. 11-15 is generally cylindrical in shape, but other shapes, such as spheroids, elipses, footballs, crescents or other shapes may be used.

As shown in FIGS. 11-15, another embodiment of the present invention 100 comprises a top surface 120 and a bottom surface 140. There is a plurality of holes passing from the top surface 120 through the device 100 and to the bottom surface 140.

As shown in FIG. 11, a trench may also be provided 220 between at least 2 of the holes 160 at the bottom surface 140. A suture may then be passed through one of the plurality of holes 160 from the top surface 120 to the bottom surface 140. The suture then may pass through a trench 220 to another of the plurality of holes 160, where it is then passed from the bottom surface 140 to the top surface 120. The trench 220 may allow the suture to be place precisely on the device and/or to slide freely through the device 100 during use. The user may use sutures through operation of a needle on one end of size PS2 or P3 or other sizes depending on the procedure being performed and the needs of the surgeon and patient.

Figure 12:
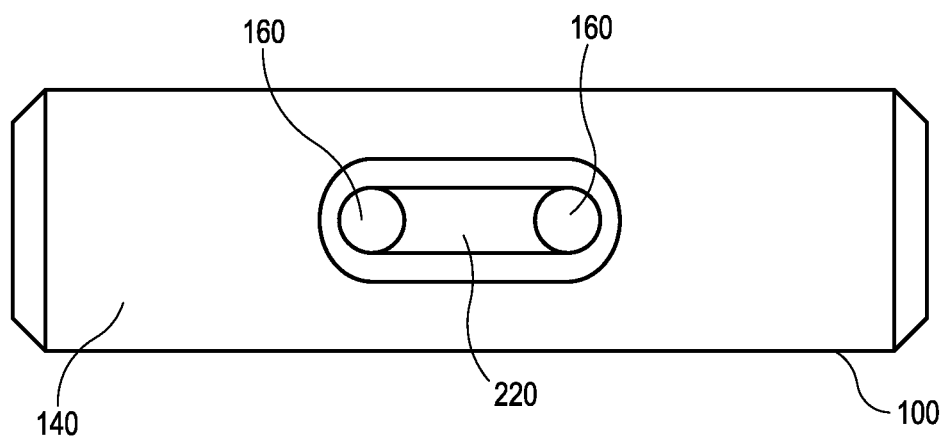
FIG. 12 is a bottom view of another embodiment of said device.
Figure 13:
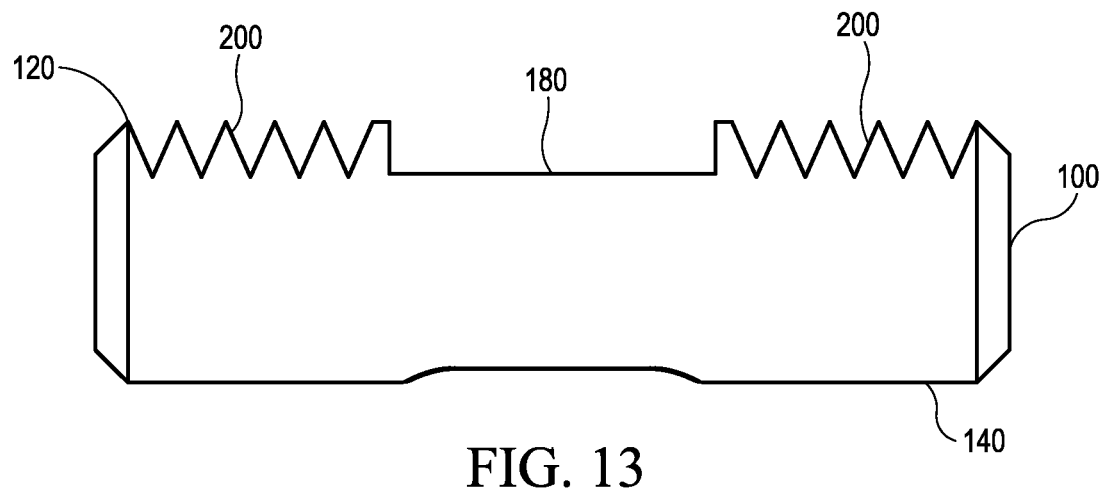
FIG. 13 is a side view of another embodiment of said device.
Figure 14:
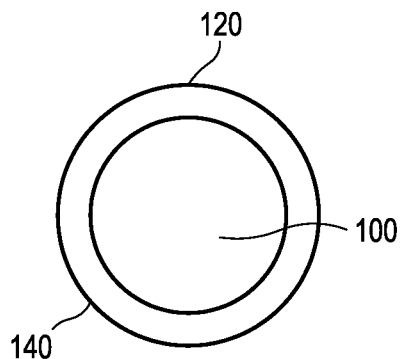
FIG. 14 is an end view of another embodiment of said device.

As shown in FIGS. 12 and 13, the top surface 120 of the device 100 has at least one geometric irregularity 200. FIG. 12 shows six irregularities 200 in the top surface 120 of the device 100, however a greater or lesser number of irregularities may be used. FIG. 13 shows the irregularities 200 as jagged edges; however, other shapes of irregularities, including trenches, ridges, multi-angled teeth, or other shapes may be used.

As shown in FIG. 12, the top surface 120 has a flat section 180 between the irregularity/ies in the surface 200. The flat section 180 may surround the plurality of holes 160. During use, tension is placed on the suture that is passed through the plurality of holes 160 from the top surface 120 to the bottom surface 140 through the trench 220 on the bottom surface 140 and then from the bottom surface 140 to the top surface 120 through the plurality of holes 160. Tension may be placed on the suture to pull the device 100 into the inner side of the wall that forms the intramedullar cavity. The irregularity/ies 200 in the top surface 120 contact the inner side of the intramedullar cavity wall. These irregularity/ies allow the device 100 to grip the inner side of the intramedullar cavity wall. The flat section 180 in the top surface 120 creates a space between the device 100 and the inner side of the intramedullar cavity wall which may allow the suture to slide more freely through the device 100 during surgery.

Figure 15:
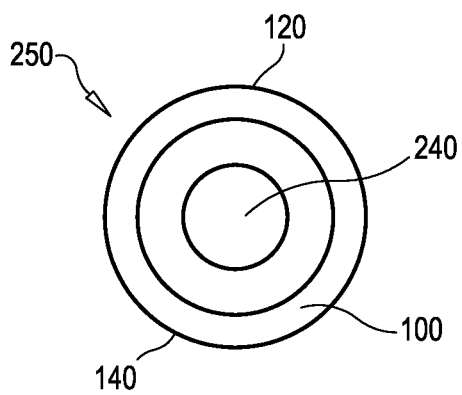
FIG. 15 is a view of the other end of another embodiment of said device.

As shown in FIG. 15, one end of the device 100 has an insertion depression 240 for use with an insertion device during implantation.

The inventors claim:

1. An intramedullary bone anchor, comprising
   a top section;
   a bottom section;
   a center section;
   a first end having a top inner portion and a top outer portion and only a single end point;
   a second end having a top inner portion and a top outer portion and only a single end point;
   a long axis running from the first end to the second end; and
   at least two holes extending from the top section through the bottom section;
   wherein the first end is tapered towards the single end point of the first end;
   wherein the second end is tapered towards the single end point of the second end;
   wherein the bone anchor is generally crescent-shaped, and the first end is upwardly curved;
   wherein the top section further includes an offset generally planar angled inserter surface inclined relative to the long axis of the apparatus located between two generally parallel surfaces between the first end and the second end;
   wherein the angled inserter surface further includes an inserter indentation.

2. The intramedullary bone anchor of claim 1, wherein the second end is upwardly curved.

3. The intramedullary bone anchor of claim 1, wherein the top outer portion of the first end contains seating enhancing geometry.

4. The intramedullary bone anchor of claim 3, wherein the seating enhancing geometry comprises at least one point.

5. The intramedullary bone anchor of claim 1, wherein the top outer portion of the second end contains seating enhancing geometry.

6. The intramedullary bone anchor of claim 1, wherein the holes are located generally near the center section of the bone anchor.

7. The intramedullary bone anchor of claim 6, wherein the holes are located along the long axis of the bone anchor.

8. The intramedullary bone anchor of claim 6, further comprising an indentation on the bottom section running between the two holes.

9. The intramedullary bone anchor of claim 1, wherein the inserter surface includes an inserter indentation.

10. The intramedullary bone anchor of claim 1, wherein the inserter indentation is complementary to a tip for an inserter.

11. A method for inserting a bone anchor into the medullary cavity of a bone, comprising the steps of:
    a) providing the intramedullary bone anchor of claim 1
    b) inserting suture material through a first hole of the at least two holes and then through a second hole of the at least two holes;
    c) inserting the intramedullary bone anchor into an opening into a medullar cavity of a bone;
    d) seating the anchor in the medullar cavity of a bone;
    e) connecting one end of the suture material to at least one of a tendon, muscle, ligament and prosthetic; and
    f) seating the at least one of a tendon, muscle, graft, ligament and prosthetic so that it abuts the opening in the medullary cavity and the periosteum around the opening.

12. The method of claim 11, wherein the step of inserting the intramedullary bone anchor into an opening into a medullar cavity of a bone further comprises the steps of:
    1) providing an inserter;
    2) placing the inserter in the inserter indentation on the intramedullary bone anchor; and
    3) using the inserter to help place the intramedullary bone anchor into an opening into a medullar cavity of the bone.

13. The method of claim 12, wherein the inserter indentation is located on the inserter surface on the intramedullary bone anchor.

* * * * *